(12) United States Patent
Wang et al.

(10) Patent No.: US 7,737,288 B2
(45) Date of Patent: Jun. 15, 2010

(54) NON-STEROIDAL ANDROGEN RECEPTOR MODULATORS, PREPARATION PROCESS, PHARMACEUTICAL COMPOSITION AND USE THEREOF

(75) Inventors: Mingwei Wang, Shanghai (CN); Caihong Zhou, Shanghai (CN); Xin Hui, Shanghai (CN); Haoran Su, Shanghai (CN); Jie Gao, Shanghai (CN); Yong Deng, Sichuan (CN); Dacheng Yang, Sichuan (CN)

(73) Assignees: Shanghai Institute of Materia Medica Chinese Academy of Sciences, Shanghai (CN); Sichuan University, Chengdu, Sichuan (CH)

( * ) Notice: Subject to any disclaimer, the term of this patent is extended or adjusted under 35 U.S.C. 154(b) by 279 days.

(21) Appl. No.: 11/921,088

(22) PCT Filed: May 26, 2006

(86) PCT No.: PCT/CN2006/001106

§ 371 (c)(1),
(2), (4) Date: Nov. 27, 2007

(87) PCT Pub. No.: WO2006/125397

PCT Pub. Date: Nov. 30, 2006

(65) Prior Publication Data

US 2008/0293808 A1     Nov. 27, 2008

(30) Foreign Application Priority Data

May 27, 2005   (CN) .................. 2005 1 0026252

(51) Int. Cl.
C07D 307/02 (2006.01)
C07C 223/00 (2006.01)
A61K 31/34 (2006.01)
A61K 31/135 (2006.01)

(52) U.S. Cl. .................. 549/494; 564/342; 564/345; 514/471; 514/649

(58) Field of Classification Search .................. 549/494; 564/342, 345; 514/471, 649
See application file for complete search history.

(56) References Cited

U.S. PATENT DOCUMENTS

| | | | |
|---|---|---|---|
| 4,277,474 A | 7/1981 | Kohda et al. |
| 4,563,454 A | 1/1986 | Kohda et al. |
| 5,686,102 A | 11/1997 | Gross et al. |
| 5,736,154 A | 4/1998 | Fuisz |
| 5,741,511 A | 4/1998 | Lee et al. |
| 5,874,451 A | 2/1999 | Glombik et al. |
| 5,886,039 A | 3/1999 | Kock et al. |
| 5,941,868 A | 8/1999 | Kaplan et al. |
| 6,197,801 B1 | 3/2001 | Lin |
| 6,258,374 B1 | 7/2001 | Friess et al. |
| 6,352,954 B1 | 3/2002 | Kobayashi |

FOREIGN PATENT DOCUMENTS

| | | |
|---|---|---|
| CN | 1199731 A | 11/1998 |
| CN | 1292792 A | 4/2001 |
| DE | 1617683 | 8/1970 |
| JP | 39-28322 B4 | 12/1964 |
| JP | 43-30298 B4 | 12/1968 |
| JP | 11-5771 | 1/1999 |
| JP | 2003-154275 | 5/2003 |
| SU | 162127 | 6/1964 |
| SU | 164614 | 8/1964 |
| WO | 2004/112690 | 12/2004 |

OTHER PUBLICATIONS

Liu Baoyou et al, "Mannich Reaction of Aldehydes, Ketones and Amines Catalyzed by Bronsted Acid Ionic Liquids", Journal of Chemical Industry and Engineering, 2004, 55(2), pp. 2043-2046, compounds of table2.
Zou Junhua "The Mannich Reaction Between 3-Nitrobenzaldehyde (3-Chlorobenzaldehyde), Aromatic Amines and Aromatic Ketones", Organic Chemistry 1996, 16, pp. 218-222, compounds 1a~1h of table 1.
Yi Lin et al, "The Mannich Reaction between Aromatic Ketones, Aromatic Aldehydes and Aromatic Amines", Synthesis, 1991, 9, pp. 717-718.
Zou Junhua et al "The Mannich Reaction Among Acetophenone, p-Methoxybenzaldehyde and Aryiamines", Journal of Southwest China Normal University, 1991, 16(1), pp. 66-70, the whole document.
Takahiko Akiyama et al, "HCI-Catalyzed Stereoselective Mannich Reaction in H20-SDS System" Letter, 2005, 2, p. 323, compounds 5, 6 of table 4.
Yang Dacheng et al, "The Mannich Reaction of 4-Methylacetophenone with Aromatic Aldehydes and Aromatic Amines", Chemical Journal of Chinese Universities, 2000, 21(11) pp. 1694-1696, compounds 1a~2h of table 1.
International Search Report for PCT/CN2006/001106 mailed Sep. 7, 2006.

*Primary Examiner*—Rita J Desai
*Assistant Examiner*—John Mabry
(74) *Attorney, Agent, or Firm*—Nixon & Vanderhye P.C.

(57) ABSTRACT

Non-steroidal androgen receptor modulating compounds of the general formula (I), their pharmaceutically acceptable salts, preparation process and pharmaceutically compositions containing the said compounds are disclosed. Such compounds of the general formula (I) or their pharmaceutically acceptable salts can be used for preparing non-steroidal medicines to treat and/or prevent conditions or diseases such as prostatic hyperplasia, prostate cancer, hirsutism, severe hormone-dependent alopecia or acne, etc. as a result of androgen receptor antagonistic activities.

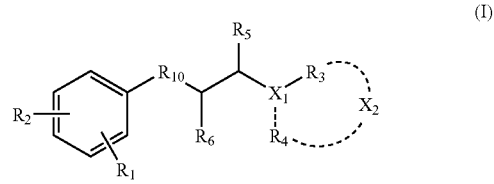

5 Claims, 3 Drawing Sheets

Structure of functional domains of androgen receptor

NON-STEROIDAL ANDROGEN RECEPTOR MODULATORS, PREPARATION PROCESS, PHARMACEUTICAL COMPOSITION AND USE THEREOF

This application is the U.S. national phase of International Application No. PCT/CN2006/001106 filed 26 May 2006 which designated the U.S. and claims priority to Chinese Application No. 200510026252.2 filed 27 May 2005, the entire contents of each of which are hereby incorporated by reference.

TECHNICAL FIELD

The present invention belongs to the pharmaceutical chemistry field, and relates to non-steroidal androgen receptor modulators, their preparation process, the pharmaceutical composition containing the non-steroidal androgen receptor modulators, and the use of the non-steroidal androgen receptor modulators in preparing medicines for preventing or/and treating the symptoms or diseases such as prostatic hyperplasia, prostate cancer, hirsutism, severe androgen-dependent alopecia and acne, etc.

BACKGROUND ART

Androgens are a category of important gonadal steroid hormones in the human body. They promote the cell differentiation and t tissue growth by binding to the corresponding specific receptors, thereby participating in many crucial physiological functions, such as the formation of genital organs of male fetus (such as prostate, seminal vesicle, epididymis, etc.), the development and maintenance of secondary sex character and the generation of sperms. In both men and women, there are a certain proportion of androgens, such as androsterone, androstanediol and adrenosterone, etc. The androgens exert important physiological effects by binding to the androgen receptors (AR). The metabolic disorder and functional disorder of androgens or their receptors may induce various diseases or promote the disease courses, including prostatic hyperplasia, prostate cancer, male sterility, hirsutism, severe androgen-dependent alopecia and acne, etc. These diseases severely influence physical and mental health of patients, as well as greatly reduce their life quality.

Benign prostatic hyperplasia is a benign adenomatous hyperplasia of cells in the region around prostate urethra, but is not a cancer. It grows slowly and will not diffuse to other parts of the body. The benign prostatic hyperplasia is one of the most common diseases in urinary surgery, and has become an "invisible killer" threatening the health of men. The clinical statistics has indicated that, the incidence of benign prostatic hyperplasia is about 50% among men with 40-79 years of age, and may reach up to 80% after the age of 80. With a an increasing pressure of modern life style, the number of benign prostatic hyperplasia patients expand gradually and the onset age has a tendency to be younger. The benign prostatic hyperplasia disturbs the daily life of patients, and it is likely to cause many kinds of latent complications, such as acute urine retention, urinary tract infection, gross hematuria, bladder diverticulum, calculus, hydronephrosis and renal failure, etc. Clinical studies in the literature indicates that dihydrotestosterone in the patient body is the foremost inducement of benign prostatic hyperplasia.

Prostate cancer is a severe disease of elderly men, the morbidity and mortality thereof are very high in the West and occupies the first place of male malignant tumors [Landis S H, Murray T, 1998, CA Cancer J. Clin. 48, 6-29]. Although the incidence of prostate cancer in China is lower than in the West, with an increase in the aging population, changes of traditional dietary structure, and improvement of diagnosis of this disease, the incidence has elevated significantly in recent years. Clinical investigations have shown that the ages of patients tend to be younger, especially among people who require long-term sitting in work, such as computer operators and taxi drivers, etc. The etiology studies and clinical therapy practices of prostatic hyperplasia/prostate cancer have attracted extensive attention in the pharmaceutical industry world-wide.

AR protein is a member of the nuclear receptor superfamily, and functions as a ligand-activated transcription factor. As shown in FIG. 1, AR protein has three structural domains: N Terminal Domain (NTD), DNA Binding Domain (DBD) and Ligand Binding Domain (LBD) [He B, Kemppainen J A, 1999, J. Biol. Chem. 274(52), 37219-25]. Androgen forms a complex with LBD of AR, and binds to an Androgen Response Element (ARE) located in the promoter region of the AR target gene to exert the function of activating or inhibiting expression of target genes, thereby regulating the physiological functions of target tissue. Prostate is an important target organ for androgen. In the embryonic period, androgen binds to AR distributing in endoderm of urinary sinus to cause phenotype differentiation of prostate epidermal cells and to induce generation of prostate-specific proteins. In mature glandular organs, androgen promotes the mitosis and proliferation of prostate epithelial cells to maintain the morphology and function of the organ [Waller A S, Sharrard R M, 2000, J. Mol. Endocrinol. 24(3), 339-351]. In addition, the androgen also regulates prostate cell metabolic activities, such as biosynthesis of lipids, and control the generation of some prostate-specific expression proteins (for example, prostate-specific antigen, PSA), and the like.

The mechanism action of androgens and AR includes a set of complicated and precise signal transduction processes, and the specific binding of androgen to AR plays an indispensable role. Many AR related diseases results from the imbalance of the interaction between androgen and AR, due to the abnormal hormone levels or receptor dysfunction. In the individuals suffering from these diseases, medicines achieve the therapeutic effects through enhancing or inhibiting the activity of AR. Therefore, with AR as a target, finding chemicals with the activity to modulate AR's functions has become a focus of global efforts. According to pharmacological properties, AR modulators can be classified as AR agonist and AR antagonist. AR antagonist is an important means for treating prostatic hyperplasia/prostate cancer (especially for advanced stages), and it competitively binds to AR in the cancerous region, blocks the uptake of androgen by cells and inhibits the effect of androgen on target organs, thereby suppressing the growth of tumor cells, decreasing the tumor volume and postponing the disease course [Leewansangtong S, 1998, Endocrine-related Cancer 5, 325-339]. Comparing with other therapies of inhibiting androgen activities, such as orchidectomy, administration of luteinizing hormone releasing hormone analogs or testosterone synthetase (for example 5α-reductase) inhibitors, AR antagonist can block the binding of androgen to AR [Hong-Chiang, C, Hiroshi M, 1999, Proc. Natl. Acad. Sci. USA 96, 11173-11177] and overcome the shortcomings of anti-androgen therapies. In addition, AR antagonist can also be used to treat some common diseases, such as hirsutism, severe androgen-dependent alopecia (baldness) and acne, etc. At present, the widely used androgen antagonists can be divided into two categories: steroidal and non-steroidal. The steroidal drugs include cyproterone acetate (CPA) and the non-steroidal ones include flutamide, nilutamide and bicalutamide (Casodex), etc.

Non-steroidal AR antagonists have high selectivity to AR and do not cause hormone-like or anti-hormone effects on other steroid receptors, so they are accepted widely in the clinic. However, all the commercially available anti-androgens have many problems to be resolved. First, patients may suffer from various side-effects after administration, such as discomfort in the gastrointestinal tract, nausea, vomiting, insomnia, hypodynamia, headache, anxiety, blurred vision and hyposexuality, etc. Second, monotherapy with anti-androgen to treat prostatic hyperplasia/prostate cancer, patients will develop anti-androgen withdrawal syndrome (AWS). It shows a quick rise of the previously inhibited PSA levels and increased tumor volume after administration for a period of time. Treatment has to cease or other anti-androgen drugs must be used [Dicker A P, 2003, Lancet Oncol. 4(1), 30-36; Laufer M, Sinibaldi V J, 1999, Urology 54(4), 745]. The molecular mechanism of AWS is still unclear, but it is generally considered that, due to gene mutation of AR in prostate cells, the drugs which originally have AR antagonistic effects may produce agonist activity on AR. Therefore, there is an unmet medical demand for AR modulators with novel chemical structures.

DISCLOSURE OF THE INVENTION

Through random high-throughput screening and subsequent structure-activity relationship studies, the present inventors synthesized and optimized a class of non-steroidal, small molecule compounds which may be divided into three series. The results from competitive receptor binding experiments indicate that the affinities of representative compounds to AR is smaller than 0.2 μM, and in a co-transfection assay with AR gene together with a luciferase reporter gene, the compounds exhibit AR antagonistic activities, with potency indicative of novel androgen receptor modulators.

Therefore, the object of the present invention is to provide a class of non-steroidal androgen receptor regulator compounds or their pharmaceutically acceptable salts having a core structure of the following general formula I.

Another object of the present invention is to provide a preparation process of the said compounds of general formula I.

Yet another object of the present invention is to provide pharmaceutical compositions containing the compounds of general formula I or their pharmaceutically acceptable salts.

The further object of the present invention is to provide the use of the compounds of general formula I or their pharmaceutically acceptable salts in preparing medicines for preventing and/or treating androgen receptor related symptoms or diseases such as prostatic hyperplasia, prostate cancer, hirsutism, severe androgen-dependent alopecia or acne, etc.

The non-steroidal androgen receptor modulating compounds or their pharmaceutically acceptable salts provided by the present invention have the structure of the following general formula I:

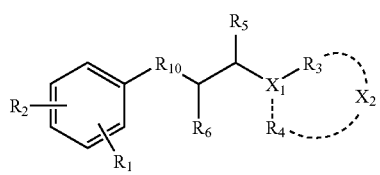

I

Wherein, $X_1$ is N, CH, O or S; and when $X_1$ is O or S, $R_4$ does not exist;

$X_2$ is O, NH or CHR, wherein R is H, C1-6 alkyl, $CF_3$, aromatic ring or aromatic heterocyclic ring;

Each of $R_1$ and $R_2$ is H, C1~6 alkyl, benzyl, halogen, OR, SR, $NR_2$, $NO_2$, CN, $CF_3$, COOR, $CONR_2$, CONHR or COR, wherein the definition of R is the same as the above;

Each of $R_3$ and $R_4$ is H, C1~6 alkyl, benzyl, C3-7 cycloalkyl optionally substituted by $R_7$, $R_8$ or $R_9$, aromatic ring optionally substituted by $R_7$, $R_8$ or $R_9$, aromatic heterocyclic ring optionally substituted by $R_7$, $R_8$ or $R_9$, or $(CHR)_n$, wherein n is an integer of 1-3, and the definition of R is the same as the above;

$R_5$ is H, C1-18 alkyl, benzyl, halogen, OR, SR, $NR_2$, $NO_2$, CN, $CF_3$, C3-7 cycloalkyl optionally substituted by $R_7$, $R_8$ and $R_9$, aromatic ring optionally substituted by $R_7$, $R_8$ and $R_9$, or aromatic heterocyclic ring optionally substituted by $R_7$, $R_8$ and $R_9$, wherein the definition of R is the same as the above; or $R_5$ can form fused ring with $R_3$;

$R_6$ is H, C1-18 alkyl, benzyl, halogen, OR, SR, $NR_2$, $NO_2$, CN, $CF_3$, aromatic ring optionally substituted by $R_7$, $R_8$ and $R_9$, or aromatic heterocyclic ring optionally substituted by $R_7$, $R_8$ and $R_9$, wherein the definition of R is the same as the above;

Wherein each of $R_7$, $R_8$ and $R_9$ is H, C1-18 alkyl, benzyl, halogen, OR, SR, $NR_2$, $NO_2$, CN, $CF_3$, COOR, $CONR_2$, CONHR or COR, wherein the definition of R is the same as the above; and $R_{10}$ is C=O, CHOH or CH=.

According to the definition of $R_{10}$, when $X_1$ is N, the compounds of the present invention are the following three series:

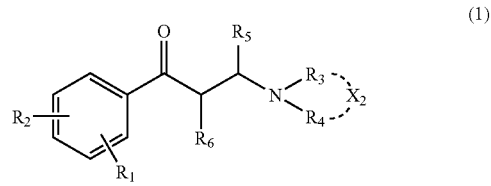

(1)

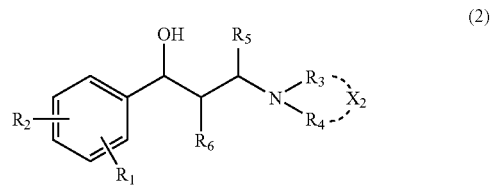

(2)

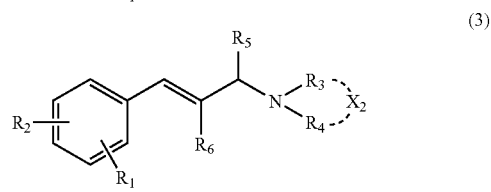

(3)

The compounds of general formula I provided by the present invention, preferably $X_1$ is N, $R_{10}$ is C=O, $R_4$ is H, $X_2$ does not exist; the structure formula of the compounds is as follows:

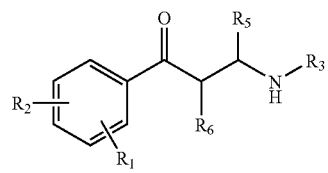

When chiral carbon exists in the molecular, the compounds represented by general formula I of the present invention are racemic or optical active compound.

When $X_1$ is N, the compounds of general formula I provided by the present invention can be prepared by the following two processes, wherein:

Preparation Process 1, which Includes the Following Steps:

Acetophenone derivatives, aromatic aldehyde or fatty aldehyde, and organic amine were used as starting materials to conduct Mannich reaction in the presence of polar solvent (such as ethanol, methanol, isopropanol, etc.) and a catalytic amount of concentrated hydrochloric acid to obtain a Mannich alkali hydrochloride, which was neutralized with a suitable quantity of base to obtain Mannich base (1); In the obtained Mannich base, the carbonyl group was reduced by catalytic hydrogenation (such as Raney Ni/$H_2$) or chemical reduction (such as $NaBH_4$, $LiAlH_4$, etc.) to obtain the compound (2); the compound (2) was dehydrated under acid catalytic condition (under catalysis of sulfuric acid, para-toluenesulfonic acid, etc; with benzene or toluene as solvent; reflux reaction) to obtain the compound (3); and the reaction flow is shown as follows:

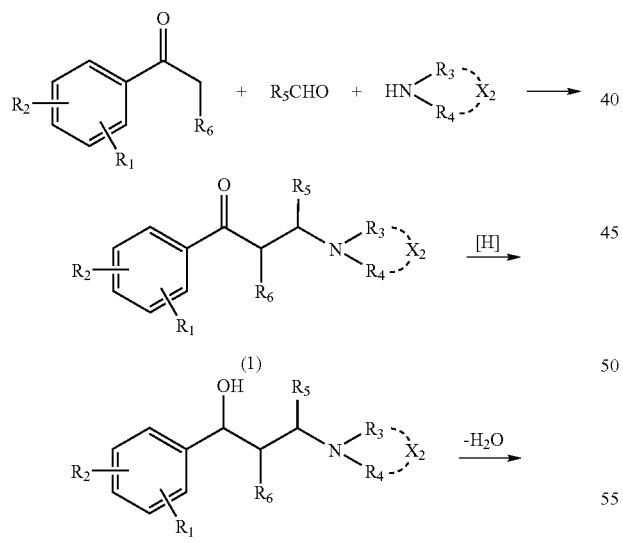

wherein the definitions of $X_2$, $R_1$, $R_2$, $R_3$, $R_4$, $R_5$ and $R_6$ are the same as the above.

Preparation Process 2, which Includes the Following Steps:

Acetophenone derivatives, aromatic aldehyde or fatty aldehyde, organic primary amine/secondary amine were used as starting materials, and in an acid or alkali condition (such as sulfuric acid, hydrochloric acid, para-toluenesulfonic acid, inorganic hydroxide, sodium alcoholate, etc.), the acetophenone derivative was condensed with the aromatic aldehyde or fatty aldehyde to produce α,β-unsaturated carbonyl compound, then under the action of catalytic amount of alkali, was subjected to Michael addition reaction with the organic primary amine/secondary amine to obtain the compound (1); In the resultant compound (1), the carbonyl group was reduced by catalytic hydrogenation or chemical reduction to obtain the compound (2); the compound (2) was dehydrated under acid catalytic condition to obtain the compound (3).

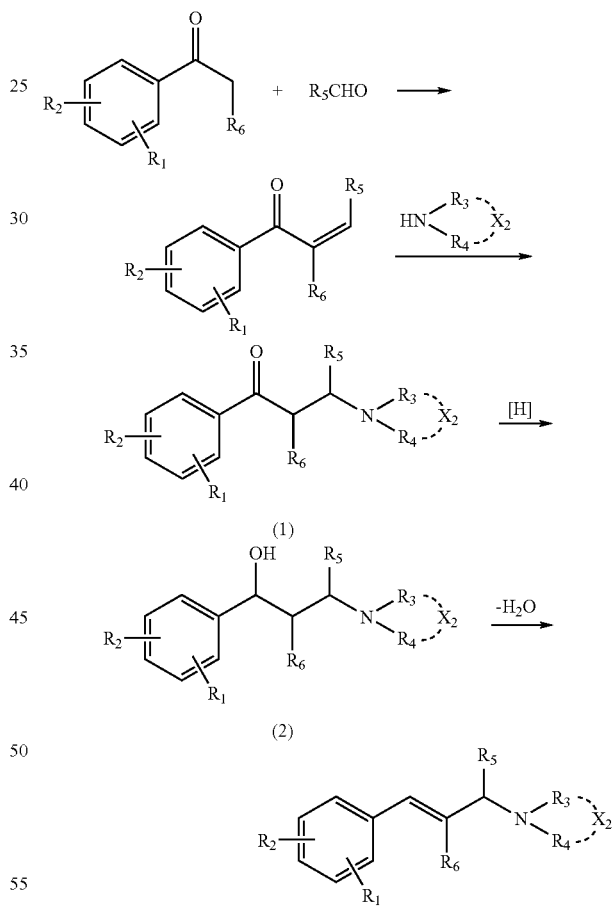

The compounds of general formula I of the present invention can be reacted with any suitable acid by common salifiable methods chemically to obtain pharmaceutically acceptable salts thereof. For example, the said acid is inorganic acid, such as hydrochloric acid, hydrobromic acid, nitric acid, sulfuric acid, phosphoric acid etc.; organic acid, such as formic acid, acetic acid, propionic acid, benzoic acid, maleic acid, fumaric acid, succinic acid, tartaric acid, citric acid etc.;

alkylsulfonic acid, such as methylsulfonic acid, ethylsulfonic acid etc.; arylsulfonic acid, such as benzenesulfonic acid, para-toluenesulfonic acid etc.

The pharmaceutical composition provided by the present invention comprises one or more therapeutically effective dose of compounds of general formula I or their pharmaceutically acceptable salts, and may further comprise one or more pharmaceutically acceptable carriers or excipients.

The ideal proportion of pharmaceutical composition provided by the present invention is that, the compounds of general formula I or pharmaceutically acceptable salts thereof as active components account for 50%-99.5% of the total weight, the rest accounts for no more than 50%.

The compounds of general formula I or their pharmaceutically acceptable salts have AR antagonistic activity, thus can be used to prepare non-steroidal medicines to prevent and/or treat symptoms or diseases such as prostatic hyperplasia, prostate cancer, hirsutism, severe androgen-dependent alopecia or acne, etc.

BEST MODE OF THE INVENTION

Figure 1:
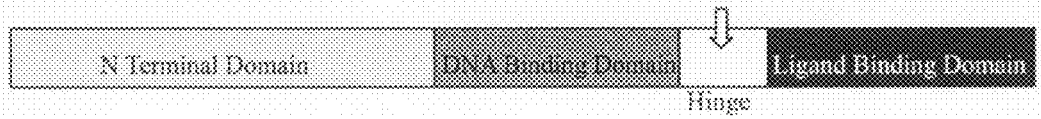
FIG. 1 is a schematic diagram illustrating the three structural domains of AR protein.

The present invention is described in detail in the following parts, but it is not to be limited thereto.

Definition

Unless otherwise defined, the technical and scientific terms used in the present invention have the same meanings according to the general comprehension in the relevant technical field. All the patents, applications, laid-open applications, and other publications and sequences from gene libraries and other databases mentioned herein are entirely incorporated by references. If the definitions interpreted in the present section are contrary to or inconsistent with the definitions included or referenced by the patents, applications, laid-open applications, and other publications and sequences from gene libraries and other databases referred by the present patent, the definitions illuminated in the present section are selected.

As used herein, "a" or "one" refers to "at least one" or "one or more".

As used herein, the "prostatic hyperplasia" refers to the benign adenomatoid hyperplasia of prostate around the urethra which may cause different levels of bladder outflow obstructive diseases or symptoms, also called "benign prostatic hypertrophy".

As used herein, the "prostate cancer" refers to the common malignant tumor of male genital system, mainly the adenocarcinoma.

As used herein, the "hirsutism" refers to the female hirsute symptoms resulted from the diseases of androgen secretion increasing. That is to say, much long, thick and dark hairs erupt in the parts where hairs should not grow, or hairs are distributed in android type, for example, the phenomenon of thick, dense and dark eyebrow, pubic hair growing to abdomen or even to umbilical part.

As used herein, the "severe androgen-dependent alopecia" refers to the severe alopecia seborrheica, also called male type alopecia.

As used herein, the "acne" refers to the pilosebaceous chronic inflammation, which frequently appears on face or chest-back, and may appear as the lesions such as acne, papule, pustule, tubercle and cyst, etc., also called youth acne.

The "effective dose" for a compound for treating certain specific disease used herein refers to a dose which can sufficiently ameliorate or alleviate to some extent the symptoms accompanied with this disease. This dose may be administered in single dose, also be administered according to a therapeutic regimen. This dose may cure diseases, or typically is administered to ameliorate the symptoms. The repeat administration for ameliorating symptoms may be needed.

As used herein, "pharmaceutically acceptable salts, esters or other derivatives" include any salts, esters or derivatives which may be prepared easily by a person skilled in the art with known process. The compounds derived and produced thus can be applied to animals and humans without any toxic effect. The compounds have drug activities, or are prodrugs.

As used herein, "treat" means the amelioration or other beneficial change of diseases and symptoms in any mode. "Treat" also includes the use of the compounds of the present invention in medicines.

As used herein, "ameliorating" the symptoms of certain specific disease by administrating certain specific pharmaceutical composition means any alleviation, regardless of permanent, temporary, chronic or temporal, may be attributed to or associated with the administration of the composition.

As used herein, "substantially pure" means sufficiently uniform, and impurity can not be detected by standard analytical methods used by a person skilled in the art for evaluating purity. The said standard analytical methods include, for example, thin layer chromatography (TLC), gel electrophoresis and high performance liquid chromatography (HPLC). Or sufficiently pure also means the detectable physical chemistry characteristics of the substance, such as enzyme activity and bioactivity, can not be altered even if the substance is further purified. The methods for purifying compounds to prepare substantially chemical pure compounds are well known by a person skilled in the art. However, substantially chemical pure compounds may be mixture of stereoisomers or isomers. In this case, further purification may increase the specific activity of the compounds.

As used herein, "prodrug" refers to a compound administered in vivo, which may be metabolized or converted into a biologically, pharmaceutically or therapeutically active form. In order to produce a prodrug, the pharmaceutically active compound will be modified so as to the active compound is generated through a metabolic process. The prodrug may be designed as a precursor which alters the metabolic stability or transportation properties, so as to mask the side effect or toxicity, improve the taste of drug or alter other characteristics. Once a pharmaceutically active compound is known, a person skilled in the art can design the prodrug of the compound by the knowledge of pharmacokinetics and drug metabolism in vivo [See *Medicinal Chemistry A Biochemical Approach*, Oxford University Press, New York, 1985, pages 388-392].

The term "substantially" same or uniform or similar may have some change in the context according to the comprehension of a person skilled in the art of the relevant technique, and generally has a sameness of at least 70%, preferably at least 80%, more preferably at least 90%, and most preferably at least 95%.

"Composition" used herein refers to any mixture, which may be solution, suspension, liquid, powder, ointment, aqueous, nonaqueous or any combination thereof.

"Combination" used herein means any combination of two or more.

The term "subject" used herein includes humans and animals, such as dogs, cats, cattles, pigs, rodents, etc. Experienced implementer should understand that the subject is suited to and would like to be treated and prevented for the diseases or symptoms caused or accompanied by functional disorder of androgen and/or androgen receptor, such as prostatic hyperplasia, prostate cancer, hirsutism, severe androgen-dependent alopecia and acne, etc.

The abbreviations of any protective groups, amino acids and other compounds used herein are consistent with the general, well-known abbreviations thereof or the biochemical denomination published by IUPAC-IUB committee, unless specially defined.

Formulation and Dosage

According to the present invention, the compounds of the present invention can be used alone or in combination with other medicines, carriers or excipients and may be formulated as preparations for any suitable administration routes, such as intracavitary injection, subcutaneous injection, intravenous injection, intramuscular injection, transdermal injection, oral or local administration. The present method may use an injection preparation, which may be administered in a form of single dose in ampoule or in a multi-dose container added with buffer. The preparation may adopt the following forms, such as suspension, solution, or emulsion in oleic or aqueous medium. The preparation may contain formulating reagents, such as suspending agent, stabilizer and/or dispersing agent. In addition, the active components in the form of powder may constitute a dosage form with suitable carriers, sterile pyrogen-free water or other solvents. Local administration of the present invention may adopt foam, gel, paste, ointment, transdermal patch or cream.

The pharmaceutical compositions and methods for administration used in the present invention may refer to, but not limited to, the contents reported by the U.S. Pat. Nos. 5,736, 154; 6,197,801B1; 5,741,511; 5,886,039; 5,941,868; 6,258, 374B1 and 5,686,102.

The dose for treatment or prevention may be varied depending on a severity of disease condition and the administration route. And the dose and frequency of administration is different according to the age, body weight, health status and individual responses of patients.

It is necessary to be pointed out (the physician also should know) that, the therapeutic dose must be terminated, discontinued or decreased according to toxicity and side-effect. On the contrary, if the clinical response is not obvious (excluding toxicity and side-effects), the doctor should appropriately adjust the therapeutic regimen by increasing the dose.

Any suitable administration routes can be adopted. The dosage forms include tablet, lozenge, bean shape capsule, dispersion, suspension, solution, capsule, film and the analogs thereof, etc.

In practical use, the compounds of the present invention, alone or in combination with other preparations, can be precisely mixed with drug carriers or excipients, such as β-cyclodextrin and 2-hydroxyl-propyl-β-cyclodextrin, according to common pharmaceutical mixing technique. According to administration requirement, common carriers, or special carriers for local or parenteral route can be used. Similar drug media, such as water, ethylene alcohol, oil, buffer, sugar, preservative, liposome, etc. which are well known by the person skilled in the art, can be used to prepare parenteral dosage forms, such as the compositions of intravenous injection or perfusion. The examples of such parenteral compositions include, but not limited to, 5% (W/V) of dextroglucose, normal saline or other solutions. The total dose of the compounds of the present invention, alone or in combination with other preparations, can be administered through intravenous injection using ampoule in a volume of from 1 mL to 2000 mL. The amount of dilution varies depending on the total dose to be administered.

The present invention also provides a kit to implement the therapeutic regimen. In the kit, effective dose of the compound of the present invention is comprised, alone or in combination with other reagents, in pharmaceutically acceptable form in one or more containers. The preferable medicine forms are the combination with sterile saline, dextroglucose solution, buffered solution or other pharmaceutically acceptable sterile liquids. As an alternative, the compositions may be lyophilized or dried. In such case, the kit contains optionally one pharmaceutically acceptable solution, preferable sterile solution in one container to form a composite, so as to recompose a solution for the object of injection. Typical pharmaceutically acceptable solutions are saline solution and dextroglucose solution.

In another embodiment, the kit of the present invention further comprises needle or syringe, preferably packaged in sterile form, for injecting the composition and/or packaged alcohol pad. The kit may optionally comprise a specification for doctors or patients.

Next, the present invention is further explained in combination with specific examples, but they do not limit the present invention.

EXAMPLE 1

The synthesis of 3-phenyl-3-(4-chloroanilino)-1-(4-methylphenyl)-1-acetone

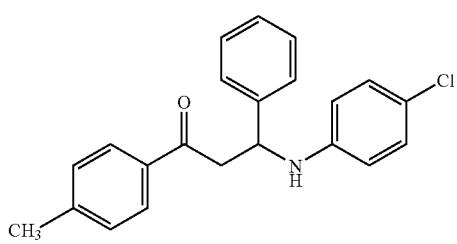

10.60 g (0.1 mol) of benzaldehyde, 12.76 g (0.1 mol) of 4-chloroaniline, 150 mL of absolute alcohol were added into a reaction bottle. After the mixture was stirred for 10 minutes at room temperature, 13.42 g (0.1 mol) of 4-methyl acetophenone and catalytic amount of concentrated hydrochloric acid were added thereinto, then the reaction was conducted for 20 hours while stirring at room temperature. After the reaction was completed, the reaction solution was cooled overnight, the separated solid was filtrated and washed with absolute alcohol. The resultant solid was suspended in 150 mL of 95% alcohol and stirred for 2 hours at room temperature. The solution was neutralized with saturated $NaHCO_3$ to basic. The stir was continued for 1 hour. The solution was filtrated, and the filter cake was washed with small amount of absolute alcohol. The crude product was recrystallized with the mixed solvent of alcohol/water (volume ratio 1:1) to obtain 25.61 g of needle crystal and the yield was 73.2%.

mp 152-154° C.; $^1$HNMR ($CDCl_3$): 7.79 (2H, d, J=8.2 Hz, Ar-H), 7.12~7.42 (7H, m, Ar-H), 7.02 (2H, d, J=8.8 Hz, Ar-H), 6.50 (2H, d, J=8.8 Hz, Ar-H), 4.92 (1H, dd, J=7.4 Hz, CH), 3.45 (2H, t, J=7.4 Hz, $CH_2$), 2.40 (3H, s, $CH_3$); MS (FAB): 350(M+H).

EXAMPLE 2

The synthesis of 3-phenyl-3-(4-bromoanilino)-1-(4-methylphenyl)-1-acetone

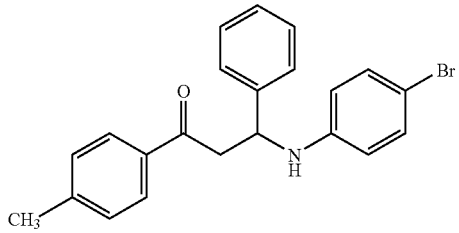

10.60 g (0.1 mol) of benzaldehyde, 17.20 g (0.1 mol) of 4-bromoaniline, 150 mL of absolute alcohol were added into a reaction bottle. After the mixture was stirred for 10 minutes at room temperature, 13.42 g (0.1 mol) of 4-methyl acetophenone and catalytic amount of concentrated hydrochloric acid were added thereinto, then the reaction was conducted for 24 hours while stirring at room temperature. After the reaction was completed, the reaction solution was cooled overnight, the separated solid was filtrated and washed with absolute alcohol. The resultant solid was suspended in 180 mL of 95% alcohol and stirred for 1.5 hours at room temperature. The solution was neutralized with saturated $NaHCO_3$ to basic, filtrated, and the filter cake was washed with small amount of absolute alcohol. The crude product was recrystallized with the mixed solvent of alcohol/water (volume ratio 1:1) to obtain 28.04 g of needle crystal and the yield was 71.1%.

mp 147-149° C.; $^1$HNMR ($CDCl_3$): 7.79 (2H, d, J=8.2 Hz, Ar-H), 7.12~7.42 (7H, m, Ar-H), 6.79 (2H, d, J=8.1 Hz, Ar-H), 6.42 (2H, d, J=8.1 Hz, Ar-H), 4.91 (1H, dd, J=7.4 Hz, CH), 3.49 (1H, d, J=7.4 Hz, $CH_2$), 3.42 (1H, d, J=7.4 Hz, $CH_2$), 2.40 (3H, s, $CH_3$); MS (FAB): 395(M+H).

EXAMPLE 3

The synthesis of 3-phenyl-3-(4-nitroanilino)-1-(4-methylphenyl)-1-acetone

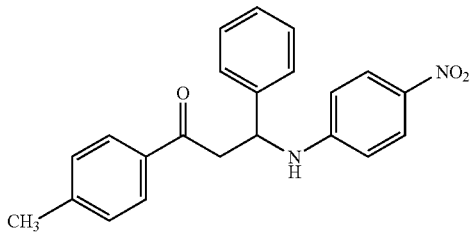

10.60 g (0.1 mol) of benzaldehyde, 13.82 g (0.1 mol) of 4-nitroaniline, 150 mL of absolute alcohol were added into a reaction bottle. After the mixture was stirred for 10 minutes at room temperature, 13.42 g (0.1 mol) of 4-methyl acetophenone and catalytic amount of concentrated hydrochloric acid were added thereinto, then the reaction was conducted for 24 hours while stirring at 32° C. After the reaction was completed, the reaction solution was cooled overnight, the separated solid was filtrated and washed with absolute alcohol. The resultant solid was suspended in 160 mL of 95% alcohol and stirred for 1.5 hours at room temperature. The solution was neutralized with saturated $NaHCO_3$ to basic, filtrated, and the filter cake was washed with small amount of absolute alcohol. The crude product was recrystallized with the mixed solvent of alcohol/water (volume ratio 1:1) to obtain 32.04 g of crystal and the yield was 88.9%.

mp 157-159° C.; $^1$HNMR ($CDCl_3$): 7.79 (2H, d, J=9.1 Hz, Ar-H), 7.78 (2H, d, J=8.4 Hz, Ar-H), 7.22~7.40 (7H, m, Ar-H), 6.50 (2H, d, J=9.1 Hz, p-$NO_2C_6H_4NH$-), 5.58 (1H, brs, NH), 5.07 (1H, t, J=5.8 Hz, CH), 3.48 (2H, d, J=5.8 Hz, $CH_2$), 2.40 (3H, s, $CH_3$); MS (FAB): 361(M+H).

EXAMPLE 4

The synthesis of 3-phenyl-3-(4-carboxylanilino)-1-(4-methylphenyl)-1-acetone

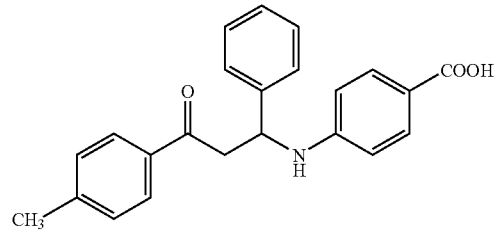

10.60 g (0.1 mol) of benzaldehyde, 13.72 g (0.1 mol) of 4-aminobenzoic acid, 140 mL of absolute alcohol were added into a reaction bottle. After the mixture was stirred for 5 minutes at room temperature, 13.42 g (0.1 mol) of 4-methyl acetophenone and catalytic amount of concentrated hydrochloric acid were added thereto, then the reaction was conducted for 20 hours while stirring at 32° C. After the reaction was completed, the reaction solution was cooled overnight, the separated solid was filtrated and washed with absolute alcohol. The resultant solid was suspended in 170 mL of 95% alcohol and stirred for 1.5 hours at room temperature. The solution was neutralized with saturated $NaHCO_3$ to basic, filtrated, and the filter cake was washed with small amount of absolute alcohol. The crude product was recrystallized with alcohol to obtain 30.59 g of crystal and the yield was 85.1%.

mp 208-210° C.; $^1$HNMR (DMSO-$d_6$): 7.86 (2H, d, J=8.2 Hz, Ar-H), 7.58 (2H, d, J=8.6 Hz, Ar-H), 6.98~7.46 (7H, m, Ar-H), 6.51 (2H, d, J=8.6 Hz, Ar-H), 5.06 (1H, m, CH), 3.24-3.35 (2H, m, $CH_2$), 2.37 (3H, s, $CH_3$); MS (FAB): 360 (M+H).

EXAMPLE 5

The synthesis of 3-(4-methylphenyl)-3-anilino-1-(4-methylphenyl)-1-acetone

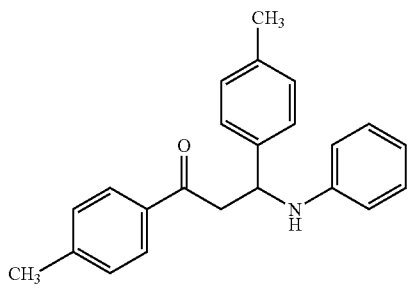

12.02 g (0.1 mol) of 4-methylbenzaldehyde, 9.31 g (0.1 mol) of aniline, 150 mL of absolute alcohol were added into a reaction bottle. After the mixture was stirred for 10 minutes at room temperature, 13.42 g (0.1 mol) of 4-methylacetophenone and catalytic amount of concentrated hydrochloric acid were added thereinto, then the reaction was conducted for 21 hours while stirring at 32° C. After the reaction was completed, the reaction solution was cooled overnight, the separated solid was filtrated and washed with absolute alcohol. The resultant solid was suspended in 160 mL of 95% alcohol and stirred for 2 hours at room temperature. The solution was neutralized with saturated $NaHCO_3$ to basic, filtrated, and the filter cake was washed with small amount of absolute alcohol. The crude product was recrystallized with alcohol/water (volume ratio 1:1) to obtain 24.05 g of crystal and the yield was 73.0%.

mp 131-132° C.; $^1$HNMR ($CDCl_3$): 7.81 (2H, d, J=8.1 Hz, Ar-H), 7.04~7.34 (9H, m, Ar-H), 6.55 (2H, d, J=7.8 Hz, Ar-H), 4.95 (1H, dd, J=6.4 Hz, 8.0 Hz, CH), 3.43 (1H, d, J=6.4 Hz, CH2), 3.41 (1H, d, J=8.0 Hz, CH2), 2.40 (3H, s, CH3), 2.30 (3H, s, CH3); MS (FAB): 330(M+H).

EXAMPLE 6

The synthesis of 3-phenyl-3-(4-chloroanilino)-1-(4-nitrophenyl)-1-acetone

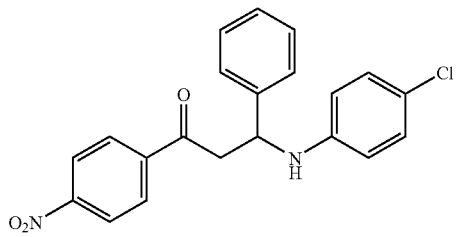

10.60 g (0.1 mol) of benzaldehyde, 12.76 g (0.1 mol) of 4-chloroaniline, 180 mL of absolute alcohol were added into a reaction bottle. After the mixture was stirred for 10 minutes at room temperature, 16.52 g (0.1 mol) of 4-nitroacetophenone and catalytic amount of concentrated hydrochloric acid were added thereinto, then the reaction was conducted for 26 hours while stirring at room temperature. After the reaction was completed, the reaction solution was cooled overnight, the separated solid was filtrated and washed with absolute alcohol. The resultant solid was suspended in 200 mL of 95% alcohol and stirred for 1 hour at room temperature. The solution was neutralized with saturated $NaHCO_3$ to basic, filtrated, and the filter cake was washed with small amount of absolute alcohol. The crude product was recrystallized with alcohol/water (volume ratio 1:1) to obtain 31.23 g of crystal and the yield was 82.0%.

$^1$HNMR ($CDCl_3$): 8.26 (2H, d, J=8.6 Hz, Ar-H), 7.99 (2H, d, J=8.6 Hz, Ar-H), 7.23-7.52 (5H, m, Ar-H), 7.04 (2H, d, J=6.4 Hz, Ar-H), 6.52 (2H, d, J=6.4 Hz, Ar-H), 4.97 (1H, t, J=6.2 Hz, CH), 3.54 (2H, d, J=6.0 Hz, $CH_2$); MS (FAB): 382(M+H).

EXAMPLE 7

The synthesis of 3-phenyl-3-(4-chloroanilino)-1-(4-methylphenyl)-1-propanol

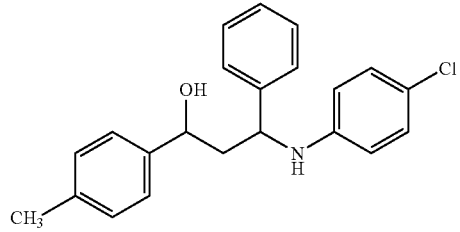

6.98 g (0.02 mol) of 3-phenyl-3-(4-chloroanilino)-1-(4-methylphenyl)-1-acetone and 120 mL of methanol were added into a reaction kettle. After the mixture was stirred at room temperature to the solid being completely dissolved, catalytic amount of Raney Ni catalyst was added thereinto. The reaction kettle was purged with hydrogen three times after it was closed tightly, then reduction was conducted for 12 hours by introducing hydrogen at 60-70° C. After the reaction was completed, the reaction solution was cooled to room temperature and filtrated, the filter cake was washed with small amount of methanol. The filtrate was distilled to remove the solvent under reduced pressure, thereby obtain a solid in powder. The resultant solid was recrystallized with alcohol/water (volume ratio 1:1) to obtain 5.80 g of crystal. The yield was 82.6%.

$^1$HNMR ($CDCl_3$): 7.81 (2H, d, J=8.4 Hz, Ar-H), 7.11-7.40 (7H, m, Ar-H), 7.03 (2H, d, J=8.2 Hz, Ar-H), 6.49 (2H, d, J=8.2 Hz, Ar-H), 5.05 (1H, t, J=7.1 Hz, CHOH), 4.94 (1H, dd, J=7.4 Hz, CH), 3.51 (2H, m, $CH_2$), 2.41 (3H, s, $CH_3$); MS (FAB): 351(M+).

EXAMPLE 8

The synthesis of 3-phenyl-3-(4-chloroanilino)-1-(4-methylphenyl)-1-propylene

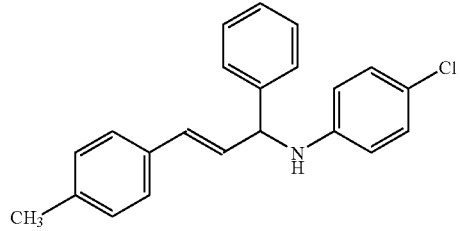

3.51 g (0.01 mol) of 3-phenyl-3-(4-chloroanilino)-1-(4-methylphenyl)-1-propanol, catalytic amount of para-toluenesulfonic acid and 80 mL of toluene were added into a reaction bottle. The reaction was conducted for 3 hours while stirring under reflux. After the reaction was completed, the reaction solution was cooled to room temperature. The toluene layer was washed with saturated $NaHCO_3$ solution and saturated salt solution in turn. The organic layer was dried over anhydrous $Na_2SO_4$, and the solvent was removed by distillation under reduced pressure. The residue was recrystallized with absolute alcohol to obtain 2.50 g of white solid. The yield was 75.1%.

$^1$HNMR ($CDCl_3$): 7.82 (2H, d, J=8.4 Hz, Ar-H), 7.16-7.42 (7H, m, Ar-H), 7.01 (2H, d, J=8.2 Hz, Ar-H), 6.63 (1H, dd, J=16.2 Hz, 7.4 Hz, CH), 6.46 (2H, d, J=8.2 Hz, Ar-H), 6.32 (1H, d, J=16.2 Hz, CH), 4.94 (1H, d, J=7.4 Hz, CH), 2.45 (3H, s, $CH_3$); MS (FAB): 334(M+H).

EXAMPLE 9

The synthesis of 3-phenyl-3-(1-piperidino)-1-(4-methylphenyl)-1-acetone

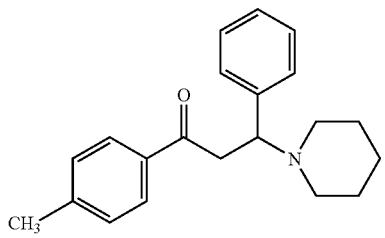

10.60 g (0.1 mol) of benzaldehyde, 8.52 g (0.1 mol) of piperidine, 150 mL of absolute alcohol were added into a reaction bottle. After the mixture was stirred for 10 minutes at room temperature, 13.42 g (0.1 mol) of 4-methylacetophenone and catalytic amount of concentrated hydrochloric acid were added thereinto, then the reaction was conducted for 18 hours while stirring at 45° C. After the reaction was completed, the reaction solution was cooled overnight, the separated solid was filtrated and washed with absolute alcohol. The resultant solid was suspended in 150 mL of 95% alcohol and stirred for 2 hours at room temperature. The solution was neutralized with saturated $NaHCO_3$ to basic and continued to be stirred for 1 hour. The solution was filtrated, and the filter cake was washed with small amount of absolute alcohol. The crude product was recrystallized with absolute alcohol to obtain 23.37 g of solid in powder. The yield was 76.0%.

$^1$HNMR ($CDCl_3$): 7.76 (2H, d, J=7.6 Hz, Ar-H), 7.12~7.42 (7H, m, Ar-H), 4.92 (1H, dd, J=7.4 Hz, CH), 3.45 (2H, t, J=7.4 Hz, $CH_2$), 2.78 (4H, m, $CH_2$), 1.55 (6H, m, $CH_2$); MS (FAB): 307(M+).

EXAMPLE 10

The synthesis of 3-phenyl-3-(1-piperidino)-1-(4-nitrophenyl)-1-acetone

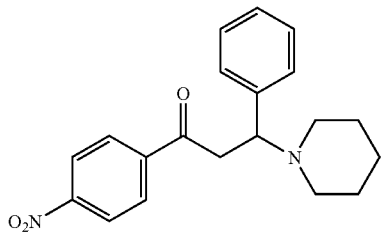

10.60 g (0.1 mol) of benzaldehyde, 8.52 g (0.1 mol) of piperidine, 180 mL of absolute alcohol were added into a reaction bottle. After the mixture was stirred for 10 minutes at room temperature, 16.52 g (0.1 mol) of 4-nitroacetophenone and catalytic amount of concentrated hydrochloric acid were added thereinto, then the reaction was conducted for 18 hours while stirring at 45° C. After the reaction was completed, the reaction solution was cooled overnight, the separated solid was filtrated and washed with absolute alcohol. The resultant solid was suspended in 150 mL of 95% alcohol and stirred for 2 hours at room temperature. The solution was neutralized with saturated $NaHCO_3$ to basic and continued to be stirred for 1 hour. The solution was filtrated, and the filter cake was washed with small amount of absolute alcohol. The crude product was recrystallized with absolute alcohol to obtain 20.31 g of solid in powder. The yield was 60.0%.

$^1$HNMR ($CDCl_3$): 8.27 (2H, d, J=8.4 Hz, Ar-H), 7.96 (2H, d, J=8.4 Hz, Ar-H), 7.18-7.49 (5H, m, Ar-H), 4.89 (1H, t, J=6.2 Hz, CH), 3.54 (2H, d, J=6.2 Hz, $CH_2$), 2.75 (4H, m, $CH_2$), 1.58 (6H, m, $CH_2$); MS (FAB): 338(M+).

EXAMPLE 11

The synthesis of 3-methyl-3-(4-chloroanilino)-1-(4-methylphenyl)-1-acetone

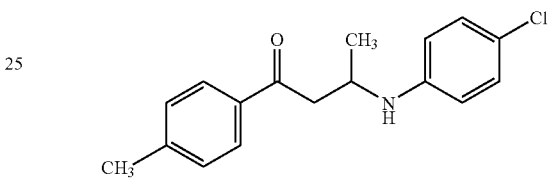

4.84 g (0.11 mol) of acetaldehyde, 12.76 g (0.1 mol) of 4-chloroaniline, 150 mL of absolute alcohol were added into a reaction bottle. After the mixture was stirred for 5 minutes at room temperature, 13.42 g (0.1 mol) of 4-methylacetophenone and catalytic amount of concentrated hydrochloric acid were added thereinto, then the reaction was conducted for 16 hours while stirring at room temperature. After the reaction was completed, the separated solid was filtrated and washed with absolute alcohol. The resultant solid was suspended in 120 mL of absolute alcohol and stirred for 1 hour at room temperature. The solution was neutralized with saturated $NaHCO_3$ to basic, filtrated, and the filter cake was washed with small amount of absolute alcohol. The crude product was recrystallized with absolute alcohol to obtain 22.45 g of solid in powder. The yield was 78.0%.

$^1$HNMR ($CDCl_3$): 7.81 (2H, d, J=8.4 Hz, Ar-H), 7.30 (2H, d, J=8.4 Hz, Ar-H), 7.05 (2H, d, J=8.6 Hz, Ar-H), 6.47 (2H, d, J=8.6 Hz, Ar-H), 4.75 (1H, m, CH), 3.43 (2H, t, J=7.4 Hz, $CH_2$), 2.40 (3H, s, $CH_3$), 2.26 (3H, d, J=6.4 Hz, $CH_3$); MS (FAB): 288(M+H).

EXAMPLE 12

The synthesis of 3-methyl-3-(4-chloroanilino)-1-(4-methylphenyl)-1-acetone

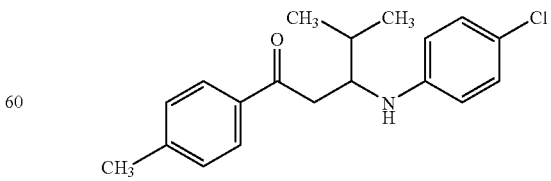

7.30 g (0.1 mol) of iso-butyraldehyde, 12.76 g (0.1 mol) of 4-chloroaniline, 150 mL of absolute alcohol were added into a reaction bottle. After the mixture was stirred for 5 minutes at room temperature, 13.42 g (0.1 mol) of 4-methylacetophenone and catalytic amount of concentrated hydrochloric acid were added thereinto, then the reaction was conducted for 20 hours while stirring at room temperature. After the reaction was completed, the separated solid was filtrated and washed with absolute alcohol. The resultant solid was suspended in 150 mL of absolute alcohol and stirred for 1 hour at room temperature. The solution was neutralized with saturated $NaHCO_3$ to basic, filtrated, and the filter cake was washed with small amount of absolute alcohol. The crude product was recrystallized with absolute alcohol to obtain 22.11 g of solid in powder The yield was 70.0%.

$^1$HNMR ($CDCl_3$): 7.82 (2H, d, J=8.4 Hz, Ar-H), 7.28 (2H, d, J=8.4 Hz, Ar-H), 7.02 (2H, d, J=8.8 Hz, Ar-H), 6.51 (2H, d, J=8.8 Hz, Ar-H), 4.75 (1H, m, CH), 3.43 (2H, m $CH_2$), 2.34 (3H, s, $CH_3$), 1.81 (1H, m CH), 0.98 (6H, d, J=6.4 Hz, $2CH_3$); MS (FAB): 316(M+H).

Bioactivity Test

1. Materials and Equipments 1.1 Plasmid and cell lines: Androgen receptor expressing plasmid and luciferase reporter gene plasmid were constructed by the National Center of Drug Screening of China; human breast cancer cell lines MDA-MB-453 and human prostate cancer cell lines LNCaP were purchased from ATCC, USA.

1.2 Reagent: Fetal bovine serum (FBS, GIBCO/BRL, USA); charcoal-dextran treated fetal bovine serum (CD-FBS, Hyclone, USA); DMEM and RPMI1640 medium (GIBCO/BRL, USA); IMEM medium (Bioresource, USA), luciferase assay kit (Promega Corporation, USA); Fugene 6 (Roche Ltd., USA); [$^3$H] dehydrotestosterone (DHT, Amersham, UK); scintillation fluid (SuperMix™, PerkinElmer, USA); androgen receptor protein was the expression product of the human androgen receptor gene expressed with the baculovirus expression system in insect cells.

1.3 Equipments: Envision 2101 Multilabel Reader (PerkinElmer, USA); $CO_2$ incubator (Form a, USA); Wallac MicroBeta® TriLux 1450 (PerkinElmer, USA); VERSA$^{max}$ Microplate Reader (Molecular Devices, USA).

2. Experimental Methods and Results 2.1 Test of Receptor Binding Activity

The solutions of DHT and each compounds of the present invention as shown in table 1 were prepared with DMSO, and the concentration gradient of DHT were 0, 0.3, 1, 3, 10, 30, 100 nM in turn, and the concentration gradient of the compounds were 0, 0.128, 0.64, 3.2, 16, 80, 400, 2000 nM in a serial order. Five µl of each dilution of DHT and the compound to be tested in different concentrations was added to each well of microtiter plates, respectively. Androgen receptor protein was added to the assay buffer (25 mM $NaPO_4$, 10% glycerol, 10 mM $NaMoO_4$, 10 mM KF, pH 7.5) provided with protease inhibitor, such as 1 µg/µl of aprotinin and leupeptin, etc., [$^3$H]DHT was added to get a final concentration of 5 nM. Then the resultant mixture was added into the plates with a volume of 195 µl each well immediately after mixed thoroughly, and incubated overnight at 4° C. After the incubation was completed, 50 µl of hydroxyapatite (HA) solution (25% HA, 25 mM $Na_3PO_4$, pH7.4) was added to each well of the calandria, uniformly mixed by shaking, and incubated for 10 minutes, during the period it was shaken once every 3 minutes. The centrifugation was conducted at 2500 rpm for 3 minutes, the supernatant was sucked out, and the precipitate was reserved. Two hundred µl of the assay buffer was added into each well, the precipitate is avoided to be shaken as far as possible, and the centrifugation was conducted for 3 minutes again. The supernatant was sucked out, and the precipitate was reserved. The centrifugation was repeated once, the supernatant was sucked out, and the precipitate was reserved. 300 µl of scintillation fluid was added to each well. The mixture was uniformly mixed by shaking, and counted with Wallac MicroBeta® TriLux 1450. As a result, nine compounds had similar affinities to androgen receptor as the positive control DHT, and their $IC_{50}$ values were below 10 nM (see Table 1).

TABLE 1

Test of binding activity to androgen receptor

| Compound | Structure | Receptor binding ($IC_{50}$, nM) |
|---|---|---|
| DHT | 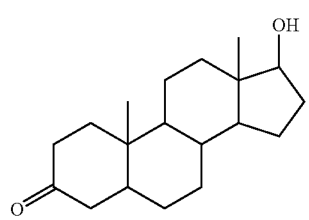 | 6.85 |
| MWW6003 | 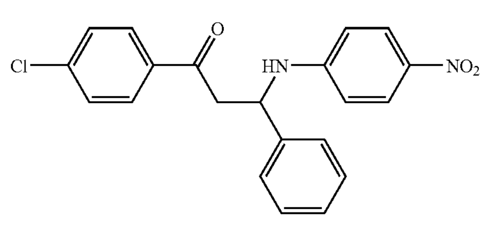 | 2.928 |

TABLE 1-continued

Test of binding activity to androgen receptor

| Compound | Structure | Receptor binding (IC$_{50}$, nM) |
|---|---|---|
| MWW6015 | 4-Br-C$_6$H$_4$-CO-CH$_2$-CH(Ph)-NH-C$_6$H$_4$-4-NO$_2$ | 2.848 |
| MWW6016 | 4-Cl-C$_6$H$_4$-CO-CH$_2$-CH(Ph)-NH-C$_6$H$_3$(4-NO$_2$)(3-CF$_3$) | 9.486 |
| MWW6021 | 4-Cl-C$_6$H$_4$-CO-CH$_2$-CH(Ph)-NH-C$_6$H$_3$(4-Cl)(3-NO$_2$) | 6.455 |
| MWW6022 | 4-Br-C$_6$H$_4$-CO-CH$_2$-CH(Ph)-NH-C$_6$H$_3$(4-Cl)(3-NO$_2$) | 4.306 |
| MWW6030 | 4-Cl-C$_6$H$_4$-CO-CH$_2$-CH(2-furyl)-NH-C$_6$H$_3$(4-Cl)(3-NO$_2$) | 3.246 |
| MWW6031 | 4-Br-C$_6$H$_4$-CO-CH$_2$-CH(2-furyl)-NH-C$_6$H$_3$(4-Cl)(3-NO$_2$) | 3.608 |
| MWW6032 | 4-Cl-C$_6$H$_4$-CO-CH$_2$-CH(2-furyl)-NH-C$_6$H$_4$-4-NO$_2$ | 2.886 |

TABLE 1-continued

Test of binding activity to androgen receptor

| Compound | Structure | Receptor binding (IC$_{50}$, nM) |
|---|---|---|
| MWW6033 | Br-C6H4-C(=O)-CH2-CH(NH-C6H4-NO2)-(furan) | 3.007 |

2.2 Test of Reporter Gene Expression

Figure 2:
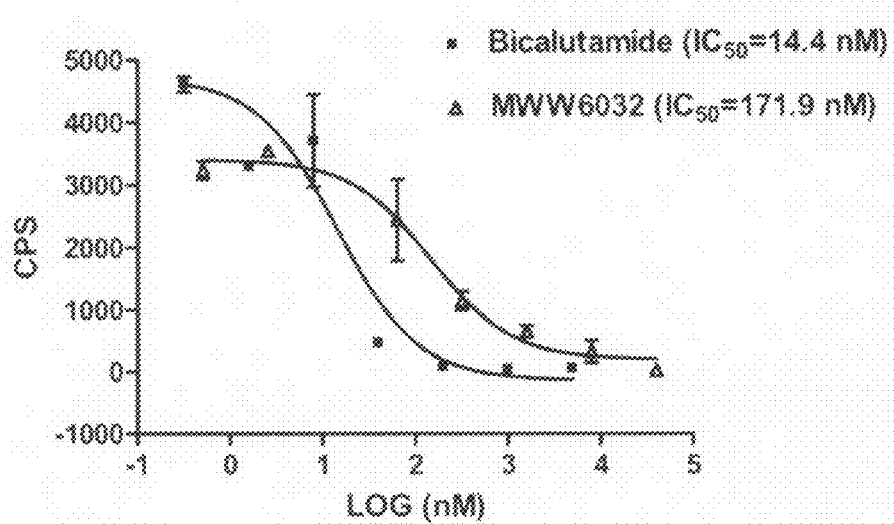
FIG. 2 shows the comparison of the activities of compound MWW6032 and bicalutamide in MDA-MB-453 cells transfected with reporter gene. Dihydrotestosterone (DHT) induces the expression of luciferase in cells so as to increase the chemiluminescence count, and decline in chemiluminescence induced by DHT indicates the antagonistic effect of the compound on androgen receptor.

MDA-MB-453 cells were cultured in IMEM medium containing 10% FBS and 2 mM L-glutamine. The above medium was replaced by IMEM medium containing 5% CD-FBS one day before transfection, and Fugene 6 reagent was used for transfection. Reporter gene vectors and Fugene 6 were uniformly mixed in a ratio of 1:3 and added to cells dropwise. The cells were cultured at 37° C. in 5% $CO_2$ for 6 hours. After the cells were dissociated, they were inoculated in a 96-well plate with 20000 cells/100 µl/well, and were cultured at 37° C. for 2 hours with IMEM medium containing 5% CD-FBS. The compounds to be tested were added thereto, the concentrations of bicalutamide were 0, 0.256, 1.28, 6.4, 32, 160, 800, 4000 nM in serial order, and the concentrations of compound MWW6032 were 0, 2.56, 12.8, 64, 320, 1600, 8000, 40000 nM in serial order. After the cells were cultured for 24 hours, luciferase assay kit was used to detect the enzyme activity, so as to evaluate the pharmacological activities of the compounds to androgen receptor. The data were shown in FIG. 2, and MWW6032 exhibited certain antagonistic activity to androgen receptor.

2.3 Test of Prostate Cancer Cell Proliferation

Figure 3:
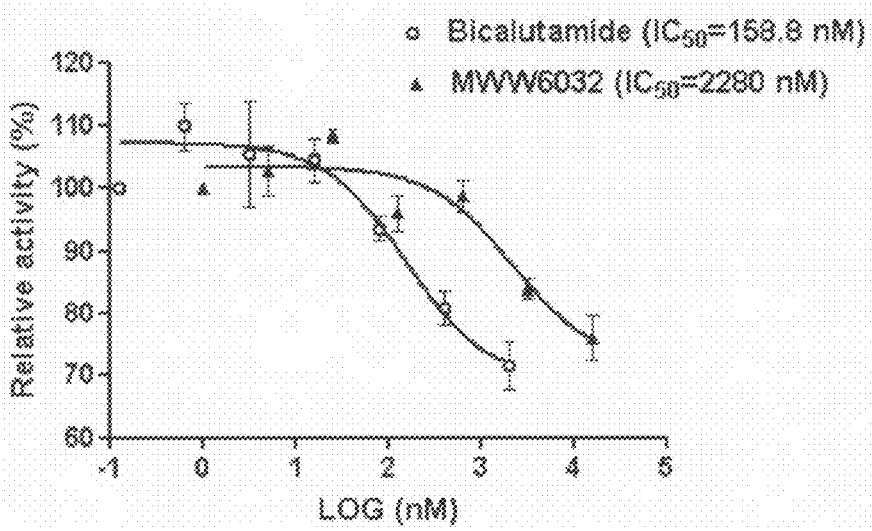
FIG. 3 exhibits the effect of compound MWW6032 and bicalutamide on LNCaP cell proliferation induced by DHT. The results show that compound MWW6032 has certain inhibitory effects on LNCaP cell proliferation stimulated by DHT, the $IC_{50}$ value thereof is 2.28 μM.

LNCaP cells were cultured in RPMI1640 medium containing 10% FBS and 2 mM L-glutamine. The above medium was replaced by RPMI1640 medium containing 5% CD-FBS one day before experiment. When the cells grew to 90% confluence, the cells were added to 96-well plate with 4000 cells/90 µL/well after dissociated with trypsin, and were cultured at 37° C. overnight. The compounds to be tested were added to the cells with 10 µL/well after diluted to certain concentrations. The concentrations of bicalutamide were 0, 0.64, 3.2, 16, 80, 400, 2000 nM in serial order, and the concentrations of compound MWW6032 were 0, 5.12, 25.6, 128, 640, 3200, 16000 nM in serial order. DHT (5 nM of final concentration) was added as an agonist thereto after the cells were incubated for 30 minutes. The cells were cultured at 37° C. for 6 days, and media containing compounds and DHT was changed once on the third day. MTT solution (5 mg/mL) was added with 20 µL/well before the culture was completed. Light absorption values at 560 nm were measured with the reference wavelength of 690 nm. The experimental data are shown in FIG. 3. The compound has certain inhibitory effect on proliferation of LNCaP cells stimulated by DHT, and the IC$_{50}$ value was 2.28 µM.

Figure 4:
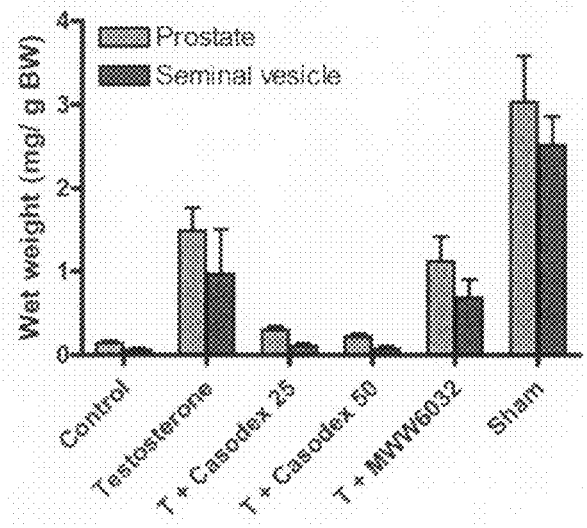
FIG. 4 and FIG. 5 show respectively the effect of compound MWW6032 and bicalutamide on wet weight and dry weight of prostate and seminal vesicle tissues from castrated rats supplemented with androgen. Casodex has significant inhibitory effects on the growth of prostate and seminal vesicle stimulated by exogenous testosterone, and compound MWW6032 displays certain inhibitory action on the growth of the above tissues under testosterone stimulation.
Figure 5:
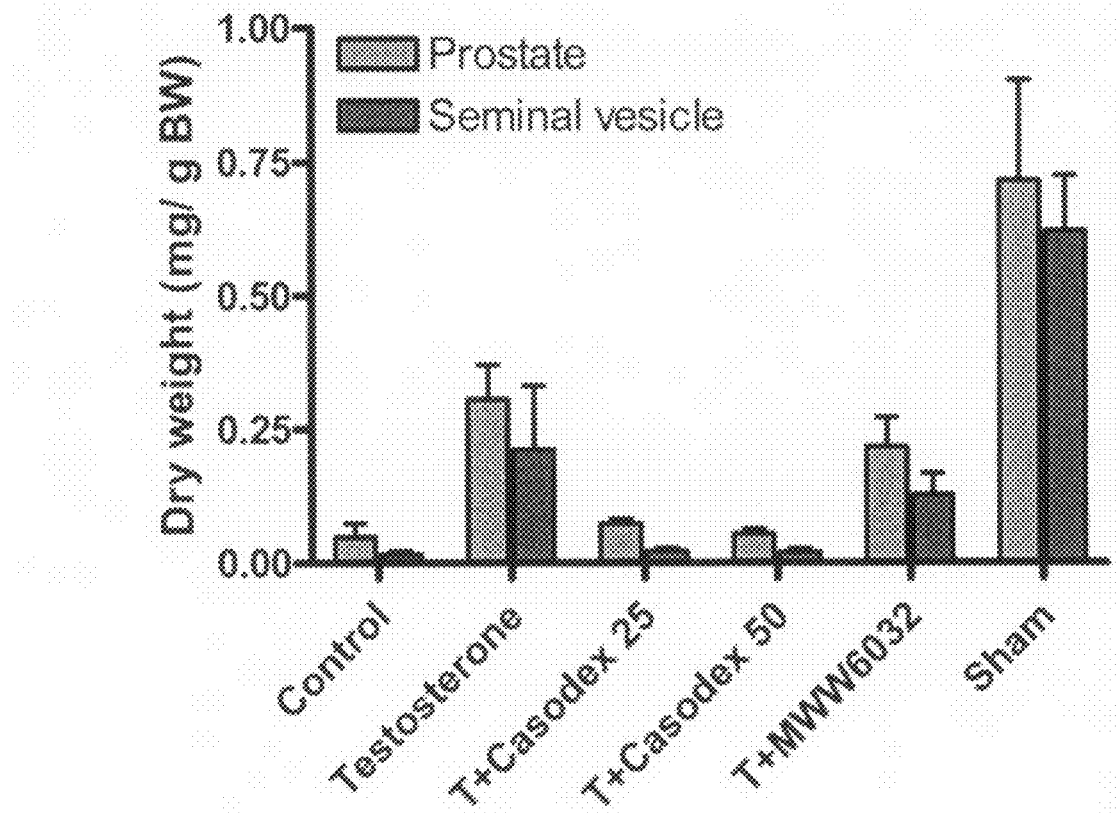

2.4 Detection of Antagonistic Activity of Compound to Androgen Receptor Using Mice 24 male SD rats of 3 weeks old were randomly divided into 6 groups, which were control group (group 1), testosterone group (group 2), testosterone(T)+bicalutamide (Casodex) 25 group (group 3), testosterone(T)+bicalutamide (Casodex) 50 group (group 4), testosterone(T)+MWW6032 group (group 5), Sham group (group 6), respectively. After the rat were accommodated for 1 week, the Sham group was sham operated, testis of the rats in the other five groups were excised (castrated). Eight weeks after the operation, the testosterone group was subcutaneously injected with 0.25 mg/kg of testosterone propionate everyday; the testosterone+Casodex 25 group was subcutaneously (s.c.) injected with 0.25 mg/kg of testosterone propionate and intragastrically (p.o.) administered with 25 mg/kg Casodex everyday; the testosterone+Casodex 50 group was administered with 0.25 mg/kg of testosterone propionate (s.c.) and 50 mg/kg Casodex (p.o.) everyday; the testosterone+MWW6032 group was subcutaneously administered with 0.25 mg/kg of testosterone propionate and intraperitoneally injected with 250 mg/kg of compound MWW6032 everyday. The rats were successively administered for 10 days. Twenty-four hours after the last administration, the rats were sacrificed, their prostate glands and seminal vesicles were taken out to measure the wet weights and dry weights. The differences between various groups were compared after body weight (BW) correction. The experimental results are shown in Table 2, Table 3, FIG. 4 and FIG. 5. Subcutaneously administered testosterone propionate (0.25 mg/kg) could produce obvious AR agonist action in castrated rats of 11 weeks old; 25 mg/kg of Casodex could antagonize the action of testosterone propionate significantly; all the prostate gland weights (PW) and seminal vesicle weights (SVW) of the rats in the compound MWW6032 group were lower than the testosterone propionate group, indicating its AR antagonistic activity in vivo.

TABLE 2

Prostate and seminal vesicle wet weights in castrated mice following anti-androgen treatment

| Group No. | Group name | Prostate weight/body weight × 1000 | Seminal vesic weight/body weight × 1000 |
|---|---|---|---|
| 1 | Control | 0.14 ± 0.03 | 0.06 ± 0.03 |
| 2 | Testosterone | 1.49 ± 0.28 | 0.97 ± 0.54 |
| 3 | Testosterone + Casodex 25 | 0.30 ± 0.04 | 0.11 ± 0.03 |
| 4 | Testosterone + Casodex 50 | 0.22 ± 0.03 | 0.07 ± 0.04 |
| 5 | Testosterone + MWW6032 | 1.12 ± 0.30 | 0.69 ± 0.22 |
| 6 | Sham | 3.03 ± 0.56 | 2.52 ± 0.34 |

TABLE 3

Prostate and seminal vesicle dry weights in castrated mice following anti-androgen treatment

| Group No. | Group name | Prostate weight/body weight × *1000 | Seminal vesic weight/body weight × *1000 |
|---|---|---|---|
| 1 | Control | 0.048 ± 0.026 | 0.016 ± 0.006 |
| 2 | Testosterone | 0.307 ± 0.065 | 0.212 ± 0.121 |
| 3 | Testosterone + Casodex 25 | 0.073 ± 0.009 | 0.022 ± 0.005 |
| 4 | Testosterone + Casodex 50 | 0.055 ± 0.006 | 0.020 ± 0.006 |
| 5 | Testosterone + MWW6032 | 0.217 ± 0.055 | 0.127 ± 0.040 |
| 6 | Sham | 0.717 ± 0.188 | 0.623 ± 0.102 |

3. Conclusion of Experiments
  (1) Compounds WMW6003, 6015, 6016, 6021, 6022, 6030, 6031, 6032 and 6033 showed potent binding affinities to the androgen receptor with $IC_{50}$ values below 10 nM, similar to that of DHT.
  (2) The above compounds (such as MWW6003 and MWW6032) displayed androgen receptor antagonistic activities with $IC_{50}$ values close to the androgen receptor antagonist bicalutamide.
  (3) Compound MWW6032 exhibited inhibitory effects on androgen=dependent proliferation of prostate cancer cell lines LNCaP, and the $IC_{50}$ value was 2.28 μM, suggesting its potential use in prostate cancer treatment.
  (4) In the castrated rat animal model, compound MWW6032 demonstrated an inhibitory profile to suppress the growth of prostate and seminal vesicles induced by exogenous testosterone propionate supplement.

The invention claimed is:

1. A compound selected from the group consisting of those of the following structure formulae:

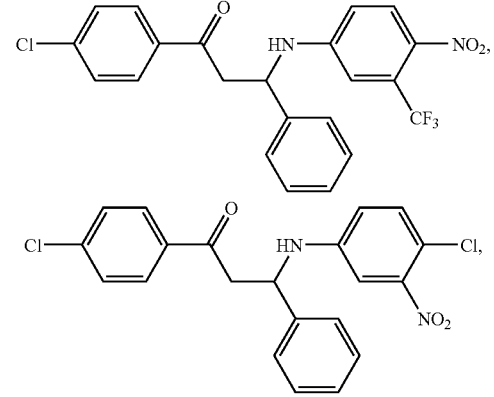

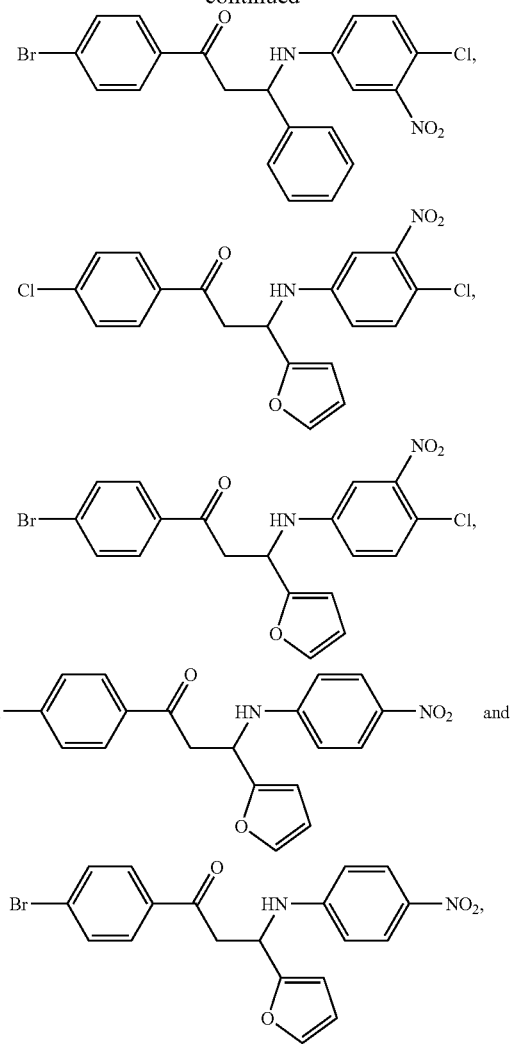

or its pharmaceutically acceptable salt.

2. The compound or its pharmaceutically acceptable salt according to claim 1, wherein the pharmaceutically acceptable salt is the salt of the compound with hydrochloric acid, hydrobromic acid, nitric acid, sulfuric acid, phosphoric acid, formic acid, acetic acid, propionic acid, benzoic acid, maleic acid, fumaric acid, succinic acid, tartaric acid, citric acid, alkylsulfonic acid, or arylsulfonic acid.

3. A pharmaceutical composition comprising one or more therapeutically effective amount of compounds or pharmaceutically acceptable salts thereof according to claim 1.

4. The pharmaceutical composition according to claim 3, further comprising one or more pharmaceutically acceptable carriers or excipients.

5. The pharmaceutical composition according to claim 3, wherein the compounds or pharmaceutically acceptable salts thereof as active component accounts for 50%-99.5% of the total weight.

* * * * *